US009737320B2

(12) United States Patent
Stopek et al.

(10) Patent No.: US 9,737,320 B2
(45) Date of Patent: Aug. 22, 2017

(54) SURGICAL GRASPER WITH INTEGRATED PROBE

(75) Inventors: Joshua Benjamin Stopek, Yalesville, CT (US); Garrett Ebersole, Southington, CT (US); Amin Elachchabi, Hamden, CT (US)

(73) Assignee: Covidien LP, Mansfield, MA (US)

( * ) Notice: Subject to any disclaimer, the term of this patent is extended or adjusted under 35 U.S.C. 154(b) by 723 days.

(21) Appl. No.: 13/028,289

(22) Filed: Feb. 16, 2011

(65) Prior Publication Data

US 2011/0230910 A1 Sep. 22, 2011

Related U.S. Application Data

(60) Provisional application No. 61/315,280, filed on Mar. 18, 2010.

(51) Int. Cl.
*A61B 17/00* (2006.01)
*A61B 17/29* (2006.01)
(Continued)

(52) U.S. Cl.
CPC ........ *A61B 17/29* (2013.01); *A61B 2090/306* (2016.02); *A61B 2090/309* (2016.02); *A61B 2090/3614* (2016.02)

(58) Field of Classification Search
CPC .... A61B 2017/2901; A61B 2017/2902; A61B 2017/2926; A61B 2017/2932; A61B 2017/2933; A61B 2017/2394; A61B 2017/2936; A61B 2017/2937; A61B 2017/2939; A61B 2017/294; A61B 2017/320044; A61B 2017/301–2017/303;
A61B 2017/305; A61B 2017/320064; A61B 17/28; A61B 17/29; A61B 17/22031; A61B 17/30; A61B 2017/00353; A61B 1/00165; A61B 10/06; A61B 10/0266;
(Continued)

(56) References Cited

U.S. PATENT DOCUMENTS 3,895,636 A 7/1975 Schmidt
4,249,533 A 2/1981 Komiya
(Continued)

FOREIGN PATENT DOCUMENTS

WO WO 98/40015 A2 9/1998
WO WO 99/30622 A2 6/1999
(Continued)

OTHER PUBLICATIONS

Partial European Search Report for EP 11250328.9-1654 date of completion is Oct. 22, 2014 (5 pages).
(Continued)

*Primary Examiner* — Melanie Tyson
*Assistant Examiner* — Erin Colello

(57) ABSTRACT

A surgical instrument for minimally invasive surgical procedures having a handle portion, an elongated body portion extending distally from the handle portion, an end effector movable between a first position and a second position, and an elongated tissue probe movably positioned within the elongated portion. The probe is movable between a retracted position and an advanced position, wherein movement of the probe moves the end effector from the first position to the second position.

13 Claims, 5 Drawing Sheets

(51) Int. Cl.
*A61B 90/00* (2016.01)
*A61B 90/30* (2016.01)

(58) Field of Classification Search
CPC . A61B 10/02; A61B 2010/0225; A61B 19/52; A61B 2019/5206; A61B 18/1442; A61B 18/1445; A61B 18/14473
USPC .......... 606/205–208, 15–16, 51–52, 43; 600/342, 478, 104, 185, 204, 217, 218, 600/219, 221
See application file for complete search history.

(56) References Cited

U.S. PATENT DOCUMENTS

| | | | |
|---|---|---|---|
| 4,557,255 A | 12/1985 | Goodman | |
| 4,598,699 A | 7/1986 | Garren et al. | |
| 4,721,116 A | 1/1988 | Schintgen et al. | |
| 4,788,966 A | 12/1988 | Yoon | |
| 4,869,268 A | 9/1989 | Yoon | |
| 4,887,612 A | 12/1989 | Esser et al. | |
| 5,082,000 A | 1/1992 | Picha et al. | |
| 5,226,908 A | 7/1993 | Yoon | |
| 5,318,589 A * | 6/1994 | Lichtman | 606/205 |
| 5,373,854 A | 12/1994 | Kolozsi | |
| 5,542,432 A | 8/1996 | Slater et al. | |
| 5,562,102 A | 10/1996 | Taylor | |
| 5,569,241 A | 10/1996 | Edwards | |
| 5,575,806 A | 11/1996 | Nakao et al. | |
| 5,611,813 A | 3/1997 | Lichtman | |
| 5,746,770 A * | 5/1998 | Zeitels et al. | 606/207 |
| 5,762,069 A | 6/1998 | Kelleher et al. | |
| 5,762,613 A * | 6/1998 | Sutton | A61B 10/06 600/564 |
| 5,820,630 A * | 10/1998 | Lind | 606/208 |
| 5,840,044 A | 11/1998 | Dassa et al. | |
| 5,843,000 A * | 12/1998 | Nishioka et al. | 600/566 |
| 5,871,453 A * | 2/1999 | Banik | A61B 10/0266 600/564 |
| 5,895,361 A | 4/1999 | Turturro | |
| 5,919,202 A * | 7/1999 | Yoon | 606/170 |
| 5,944,728 A * | 8/1999 | Bates | A61B 17/221 604/264 |
| 5,951,488 A * | 9/1999 | Slater | A61B 10/06 600/564 |
| 6,066,102 A * | 5/2000 | Townsend | A61B 10/06 600/104 |
| 6,110,127 A | 8/2000 | Suzuki | |
| 6,129,683 A * | 10/2000 | Sutton et al. | 600/564 |
| 6,139,508 A * | 10/2000 | Simpson et al. | 600/564 |
| 6,142,957 A | 11/2000 | Diamond et al. | |
| 6,149,607 A * | 11/2000 | Simpson et al. | 600/567 |
| 6,296,608 B1 * | 10/2001 | Daniels | A61B 1/00165 600/104 |
| 7,169,167 B2 * | 1/2007 | Chu | 606/205 |
| 7,762,959 B2 | 7/2010 | Bilsbury | |
| 7,775,989 B2 * | 8/2010 | Nakao | 600/564 |
| 8,409,243 B2 * | 4/2013 | Chu | 606/205 |
| 2007/0135686 A1 * | 6/2007 | Pruitt, Jr. | A61B 17/0218 600/214 |
| 2007/0299468 A1 * | 12/2007 | Viola | 606/205 |

FOREIGN PATENT DOCUMENTS

WO  WO 2006/096169 A1  9/2006
WO  WO 2009/111717 A1  9/2009

OTHER PUBLICATIONS

European Search Report dated May 8, 2015 issued in European Application No. 11250328.
European Office Action issued in corresponding European Appln. No. 11250328.9 dated Feb. 7, 2017.

* cited by examiner

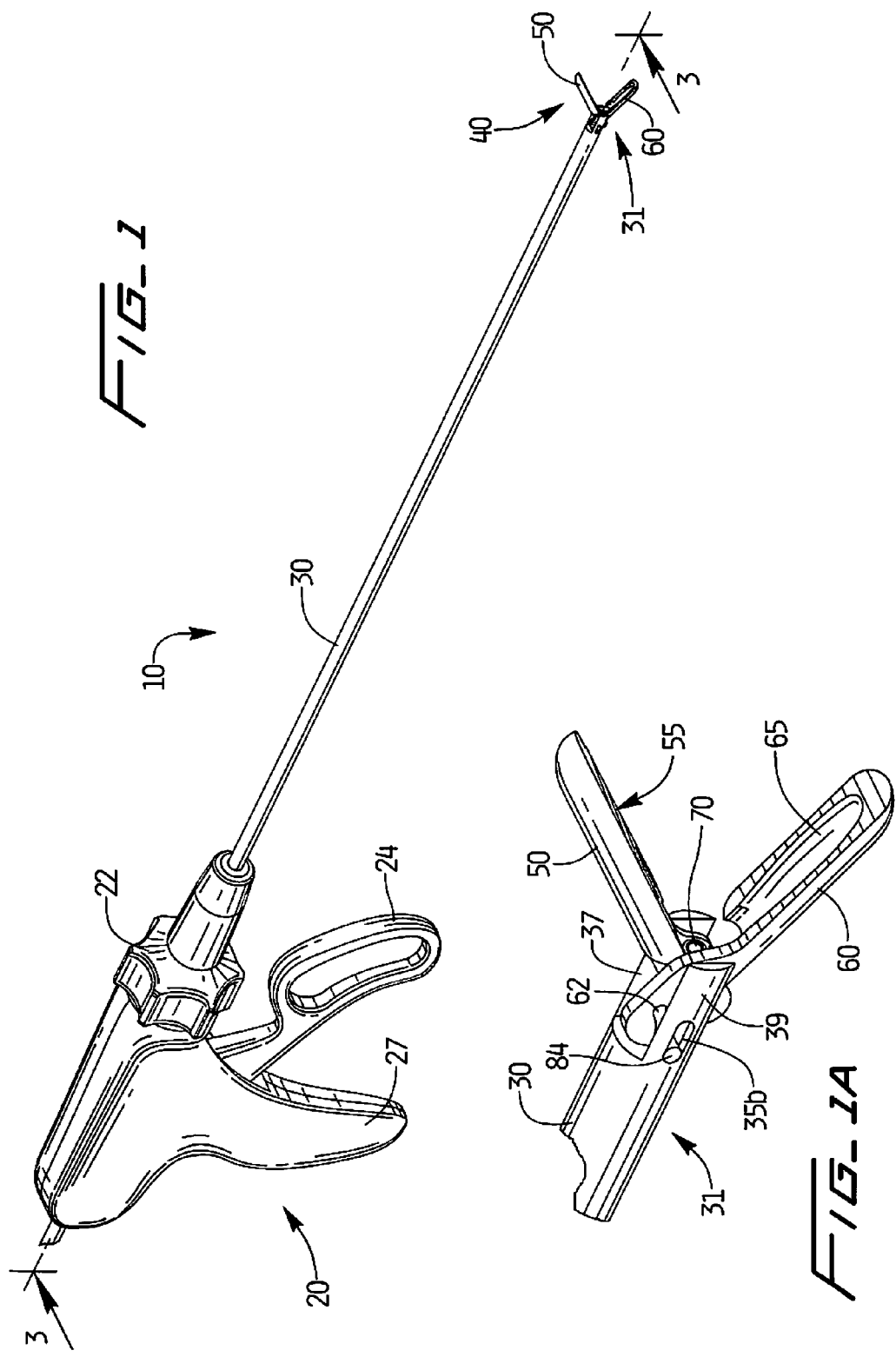

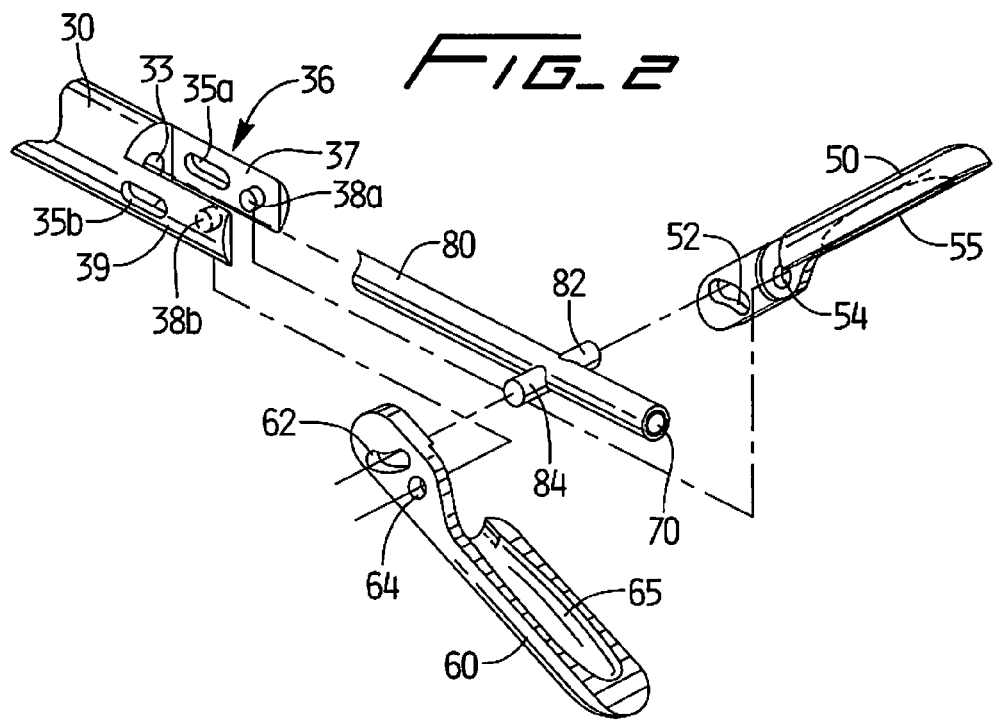
FIG_2
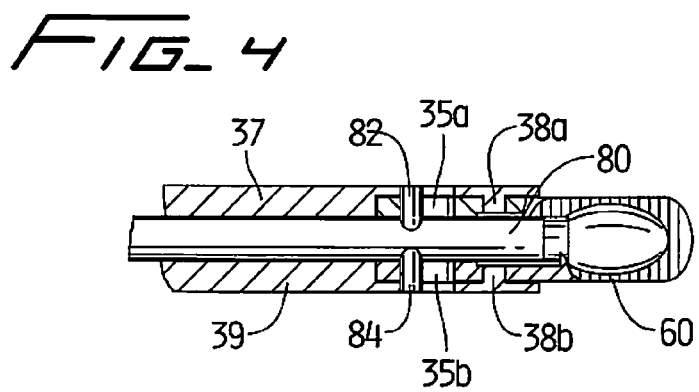
FIG_4
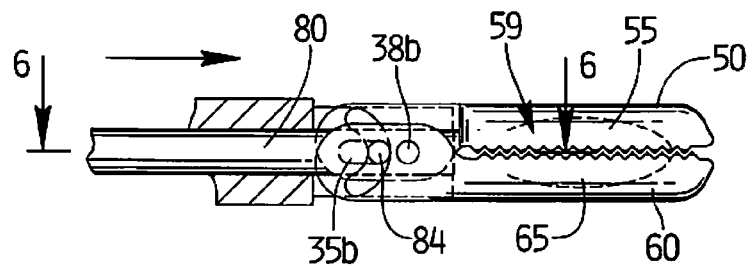
FIG_5

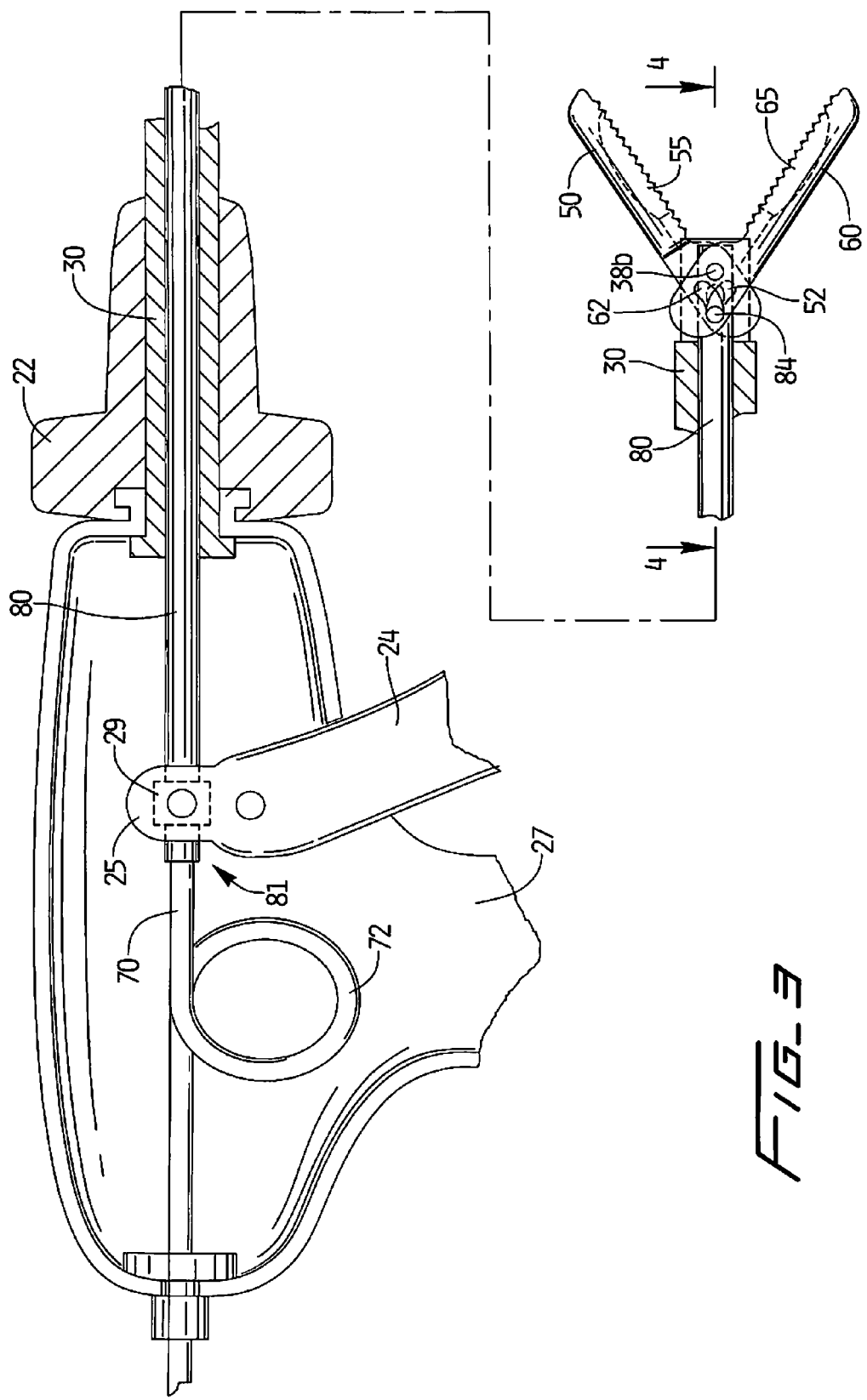

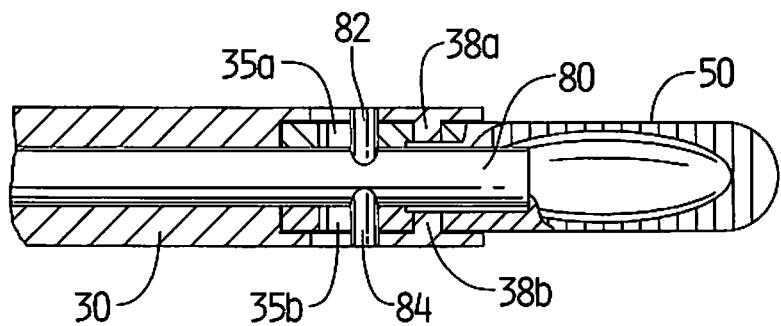
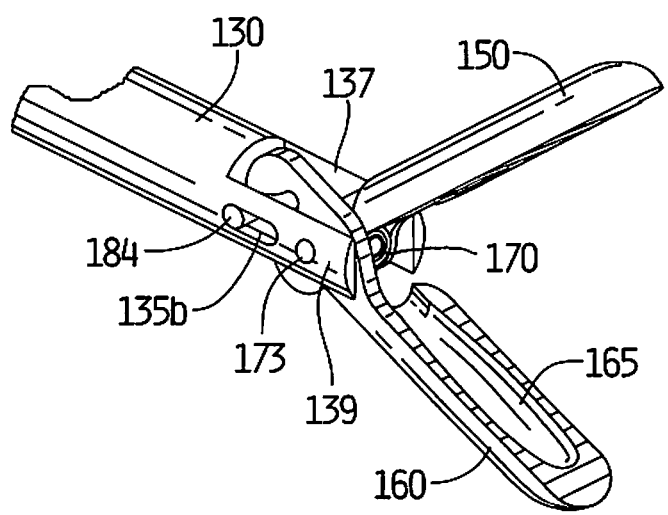

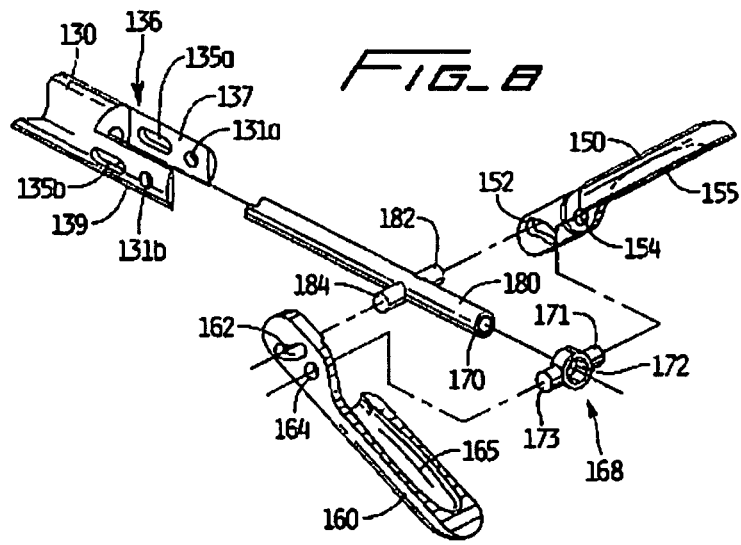
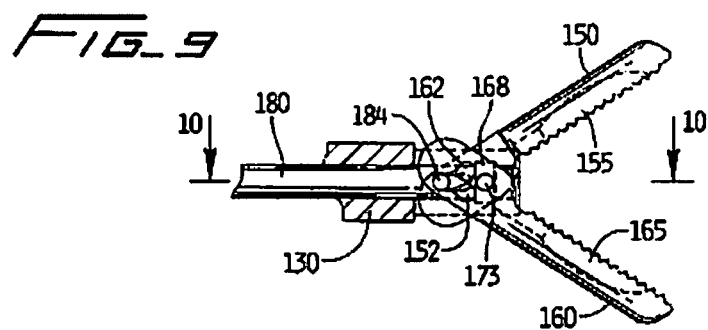
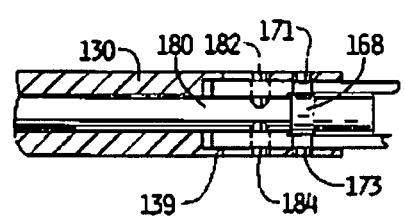

SURGICAL GRASPER WITH INTEGRATED PROBE

This application claims priority from provisional application Ser. No. 61/315,280, filed Mar. 18, 2010, the entire contents of which are incorporated herein by reference.

BACKGROUND

Technical Field

The present disclosure relates generally to a laparoscopic surgical instrument and more particularly to a surgical grasping instrument with an integrated probe.

Background of Related Art

In laparoscopic surgery, surgery is performed through access ports extending into the abdominal cavity. The advantages of laparoscopic and other minimally invasive surgical procedures are well established and include reduced infection, reduced costs and reduced patient recovery time. In many of these procedures, several access ports are required, each dimensioned to receive a surgical instrument, providing a guide for accessing the surgical site. One of the access ports is configured to receive an endoscopic camera for viewing the abdominal cavity and enabling display of the cavity and the manipulation of the instrumentation and tissue within the body cavity on a video monitor.

It would be advantageous to reduce the number of access ports in the abdominal cavity while maintaining the same instrumentation and maneuverability of the instruments within the body cavity. It would also be advantageous to alternatively provide the same number of access ports but enable use of additional instrumentation within the body cavity.

Further, during laparoscopic procedures, it would be advantageous to investigate the tissue grasped by a grasping instrument to determine desired characteristics of the tissue or to treat the tissue confined within the grasping instrument without requiring access through another port. Additionally, it would be advantageous in certain instances to provide a darkened background area within the body cavity for diagnosis or imaging of the target tissue.

SUMMARY

The present disclosure provides in one aspect a surgical instrument for minimally invasive surgical procedures comprising a handle portion, an elongated body portion extending distally from the handle portion, an end effector extending distally of the elongated body portion and movable between a first position and a second position, and an elongated tissue probe movably positioned within the elongated portion. The probe is movable between a retracted position and an advanced position, wherein movement of the probe moves the end effector from the first position to the second position.

In some embodiments, the end effector comprises first and second jaws, wherein at least one of the jaws has a cavity to receive tissue therein. In a preferred embodiment, movement of the probe to the advanced position effects movement of the end effector to the second position which is a closed position of the first and second jaws.

In some embodiments, a sheath for receiving at least a portion of the probe therein is provided. The sheath in some embodiments can include a camming member(s) engageable with a camming slot of the end effector to move the end effector between the first and second positions.

In some embodiments, the probe is a light emitting illumination probe. In other embodiments, the probe is a visualization probe for imaging the tissue captured within the cavity of the jaws. In other embodiments, the probe is a detection probe for determining characteristics of tissue. The probe can also include both illumination, visualization and/or detection functions.

The end effector in some embodiments can include first and second jaws forming a cavity therebetween when in the closed position to retain tissue therein and block out external light.

In another aspect of the present disclosure a surgical instrument is provided for minimally invasive surgical procedures comprising an actuator, an elongated portion extending distally from the actuator, and first and second jaws. At least one of the jaws has a tissue receiving cavity formed therein. A probe is movably positioned within the elongated portion for one or more of imaging, diagnosis, treatment of tissue positioned within the cavity when the first and second jaws are in a closed position.

In some embodiments, movement of the jaws to the closed position forms a substantially enclosed cavity and moves the probe from a retracted position to an advanced position. The probe in some embodiments can be contained within a sheath operatively connected to the actuator, wherein movement of the sheath from a proximal position to a distal position moves the probe from a retracted position to a distal position.

The probe is preferably operably connected to the actuator wherein actuation of the actuator moves the probe between the retracted and advanced positions.

In some embodiments, the first and second jaws are pivotally attached and both jaws are movable between an open and closed position.

In another aspect, the present disclosure provides a method for performing minimally invasive surgery comprising:

providing a grasping instrument having at least one movable jaw;

positioning the at least one movable jaw adjacent target tissue;

closing the at least one jaw to form a cavity and to automatically deliver a tissue probe to target tissue; and applying energy from the probe to the tissue.

In some embodiments, light energy is applied from the probe and the probe is a fiber optic probe. In other embodiments, the probe is an imaging probe to visualize tissue within the cavity. In other embodiments, the probe is a diagnostic probe to diagnose tissue within the cavity.

BRIEF DESCRIPTION OF THE DRAWINGS

Various embodiments of the presently disclosed device are described herein with reference to the drawings, wherein:

FIG. 1 is a perspective view of one embodiment of the grasping instrument of the present disclosure showing the jaws in the open position;

FIG. 1A is a perspective view of the jaws of the instrument of FIG. 1 in the open position;

FIG. 2 is an exploded view of the jaw assembly of FIG. 1;

FIG. 3 is a longitudinal cross-sectional view taken along line 3-3 of FIG. 1;

FIG. 4 is a cross-sectional view taken along line 4-4 of FIG. 3;

FIG. 5 is a side view in partial cross-section illustrating the jaws in the closed position with the probe in the advanced position;

FIG. 6 is a cross-sectional view taken along line 6-6 of FIG. 5;

FIG. 7 is a perspective view of an alternate embodiment of the jaw assembly of the present disclosure illustrating the jaws in the open position with the probe in the retracted position;

FIG. 8 is an exploded view of the jaw assembly of FIG. 7;

FIG. 9 is a side view in partial cross-section of the jaws of FIG. 7 in the open position and the probe in the retracted position; and FIG. 10 is a cross-sectional view taken along line 10-10 of FIG. 9;

DETAILED DESCRIPTION OF EMBODIMENTS

The surgical instrument of the present disclosure will now be described in detail with reference to the drawings in which like reference numerals designate identical or corresponding elements in each of the several views. Throughout this description, the term "proximal" will refer to the portion of the instrument closer to the operator and the term "distal" will refer to the portion of the instrument further from the operator. The presently disclosed surgical instrument is particularly suited for laparoscopic surgery but the system can be utilized for other minimally invasive surgical procedures.

The surgical instrument of the present disclosure is designated generally by reference numeral 10 and includes, with reference to FIG. 1, a handle portion 20, an endoscopic or elongated tubular portion 30 extending distally from the handle portion and an end effector 40. End effector 40 extends from a distal portion 31 of elongated portion 30. A rotation knob 22 can be provided to rotate the endoscopic portion 30 and attached end effector 40 about the longitudinal axis of the endoscopic portion 30 to reorient the end effector 40.

The end effector 40 includes a pair of jaws 50, 60, which function as tissue graspers and are pivotally mounted for movement between an open spaced apart position and a closed approximated position to capture tissue in the manner described below. Although in the illustrated embodiment both jaws 50, 60 move between open and closed positions, it is also contemplated that one of the jaws could be stationary and the other jaw movable between open and closed positions. The jaws 50, 60 can have teeth about their periphery to enhance their grasping function.

With reference to FIGS. 1, 1A and 2, jaw 50 includes a cam slot 52 and a pivot hole 54. Similarly, jaw 60 includes a cam slot 62 and a pivot hole 64. An elongated tissue probe 70 is slidably mounted within the endoscopic portion 30. More specifically, the probe 70 is fixed within a sheath 80 which is slidably mounted within a lumen in the endoscopic portion 30 and exits through distal opening 33 of the lumen of the endoscopic portion 30. Sheath 80 includes transverse posts or pegs 82, 84 which engage cam slots 52, 62, of jaws 50, 60, respectively. Consequently, movement of sheath 80 by the handle mechanism as described below moves the sheath 80 and encased probe 70 distally as well. Endoscopic portion 30 terminates in yoke 36 with parallel arms 37, 39 having inwardly extending posts 38a, 38b, respectively. Posts 38a, 38b engage pivot holes 54, 64 of jaws 50, 60 respectively. Longitudinal slots 35a, 35b of arms 37, 39 receive posts 82 and 84 of sheath 80 to accommodate sliding movement of sheath 80. Probe 70 preferably terminates at the distal end of sheath 80 but alternatively could terminate distal of the distal end of the sheath 80 so it protrudes from the sheath 80.

Jaws 50 and 60 each have a cavity 55, 65, respectively, illustratively substantially elliptical in shape, dimensioned and configured to capture target tissue. In the closed position, the cavities 55, 65 form a closed cavity 59 (FIG. 5) which can block external light to enhance illumination of the tissue specimen within the cavity 59 if an illumination probe e.g. fiber optic, is utilized. The cavity 59 as shown has a substantially oval configuration, although other configurations for the tissue capturing retaining cavity, e.g. spherical, cup shape, etc. are also contemplated.

Movement of sheath 80 functions to open and close the jaws 50, 60. More specifically, movement of the sheath 80 moves the encased and attached probe 70 from a retracted position of FIG. 1A to an advanced position of FIGS. 5 and 6 and moves the jaws 50, 60 to a closed position as transverse posts 82, 84 of sheath 80 engaged within cam slots 52, 62 cam jaws 50, 60 toward one another about posts or pins 38a, 38b of arms 37, 39. Posts 82, 84 also move distally within longitudinal slots 35a, 35b of arms 37, 39. In this manner, when the jaws 50, 60 are closed to capture tissue within the cavity 59, the probe 70 is in its advanced position to illuminate, image, diagnose and/or treat the tissue specimen captured and retained therein. Thus, advancement of the probe 70 to its operative position occurs automatically with jaw closure. Stated another way, the closing of the jaws 50, 60 automatically advances the tissue probe 70 to an advanced position adjacent the target tissue contained within the jaw cavity. The probe 70 in one embodiment is in the form of a fiber optic bundle. Alternatively, it could be a digital sensor. The probe can also be a multi-functional probe to perform more than one function. For example, it could perform both illumination and visualization or both illumination and detection. For performing both illumination and visualization it could for example have an LED for illumination and some form of a confocal or camera. The probe may be wired or wireless and information can be accessed from the device itself or by using integrated operating room systems (computer/TV monitors, surgical navigation systems, etc.).

When the probe 70 is retracted by retraction of sheath 80, the jaws 50, 60 are moved back to their open position due to the engagement of transverse posts 82, 84 within cam slots 52, 62 of jaws 50, 60 causing the jaws 50, 60 to move in the reverse direction. Note posts 82, 84 move proximally within longitudinal slots 35a, 35b of endoscopic portion 30.

The sliding movement of the probe 70 between advanced and retracted positions is achieved by the operable connection of the sheath 80 with pivotable handle 24 of handle portion 20 as shown in FIG. 3. That is, yoke 25 of pivotable handle or trigger 24 is fixedly secured to a proximal end 81 of sheath 80 via connecting block 29. Pivotal movement of handle 24 in a proximal direction, i.e. towards stationary handle 27, advances sheath 80 and attached probe 70 distally. As sheath 80 is advanced, transverse posts 82, 84 advance distally within longitudinal slots 35a, 35b of arms 37, 39 of endoscopic portion 30 and cam jaws 50, 60 to a closed position due to their engagement with respective cam slots 52, 62. Note the probe 70 can be flexible and formed into a loop portion 72 as shown in FIG. 3, which would somewhat straighten as advanced. As noted above, in the advanced position of the probe 70, the jaws 50, 60 form a closed cavity for the tissue specimen, and the probe 70 can then be utilized to illuminate, image, diagnose and/or treat tissue.

After use of the probe 70 in the surgical procedure, the instrument 10 can be withdrawn through the access port with the jaws 50, 60 maintained in the closed position and withdrawing the tissue specimen encapsulated in cavity 59 formed by cavities 55, 65 of jaws 50, 60 respectively.

If it is desired to release the specimen from the jaws within the surgical site, e.g. after an in situ diagnostic function of probe 70, the jaws 50, 60 can be opened by return of handle 24 to its original more distal position. That is, return of handle 24 to its distal position causes sheath 80 and attached probe 70 to retract (move proximally).

In the alternate embodiment of FIGS. 7-10, a grasping mechanism is provided similar to the embodiment of FIGS. 1-6, except instead of transverse posts on the arms of the endoscopic portion, an eyehole hinge 168 is provided. More specifically, jaws 150 and 160 are identical to jaws 50 and 60 and have cam slots 152, 162 and pivot holes 154, 164. Jaws 150 and 160 also have cavities 155, 165 like cavities 55 and 65 of the instrument of FIG. 1 which together when closed form a tissue capturing or retaining cavity. Endoscopic portion 130 is also identical to endoscopic portion 30 of FIG. 1 except that instead of transverse posts on its arms to engage pivot holes of the jaws, it has openings 131a, 131b on arms 137, 139 of yoke 136 to receive the transverse posts 171, 173 of eyehole hinge 168. Hinge 168 has an opening 172 through which the probe 170 and sheath 180 travel through. It also forms the pivot point for the jaws 150, 160 and holds the two sides of the jaws 150, 160 in place.

The grasping jaws of FIGS. 7-10 operate similar to the instrument 10 in that actuation of the instrument handle will advance the sheath 180 distally to cam the jaws 150, 160 to the closed position via the engagement of transverse posts 182, 184 and cam slots 152, 162, of jaws 150, 160, respectively. Transverse posts 182, 184 slide distally within longitudinal slots 135a, 135b of arms 137, 139. Advancement of the sheath 180 to close the jaws 50, 60 carries the attached probe 170 distally for use within the cavity formed by cavities 155, 165 of the closed jaws 150, 160. Thus, as in the embodiment of FIG. 1, movement of the jaws 150, 160 to the closed position and movement of the probe 170 (and sheath 180) to the advanced position occur substantially simultaneously. Note probe 170 and sheath 180 can be in the same form as probe 70 and sheath 80 described herein.

To open the jaws 150, 160, as in the embodiment of FIG. 1, the handle is returned to its distal position, thereby moving sheath 80, and attached probe 70, proximally such that transverse posts 182, 184 travel proximally within longitudinal slots 135a, 135b and force the jaws 150, 160 to the open position due to their engagement with cam slots 152, 162.

As can be appreciated, the delivery of the probe in the foregoing embodiments is achieved automatically as the instrument jaws are moved to a closed position.

In a preferred embodiment, the probe 70 (or 170) has a diameter of about 3 mm or less, although other dimensions are also contemplated. The probe can be, for example, a confocal fluorescence microscope probe, a near infrared Raman spectroscopy probe, an auto-fluorescence probe, a dye assisted fluorescence probe, etc. Tissue could thereby be diagnosed, illuminated, imaged and/or treated during a surgical procedure. Advancement of the probe can place it adjacent, and if desired, in contact with, the target tissue contained within the cavity formed by jaw cavities 55, 65 (or jaw cavities 155, 165).

The probe and sheath in some embodiments can be in the form or a fiber bundle surrounded by a sheath. In such embodiments, or other embodiments wherein the probe is encased or positioned within a sheath (and attached to the sheath), the sheath contains the transverse posts or other structure for moving, e.g., pivoting, the jaws between the open and closed positions. In other embodiments, where the probe is not contained within a sheath, the probe can have transverse posts or other structure to engage and move, e.g. pivot, the jaws between open and closed positions.

It should be appreciated that although pin/cam slot arrangements are shown to close the jaws, other structure to achieve opening and closing the jaws is also contemplated. Also, structure can be provided to move the jaws between open and closed positions in substantially parallel movement.

The probe can be used with biopsy jaws, grasping jaws with or without teeth as well as other jaw configurations. As noted above, the jaws can have different shaped cavities. Also, although shown as forming a closed cavity, partially open cavities are also contemplated.

The actuator for movement of the jaws and probe are shown in the form of a trigger, however, other actuators are also contemplated.

In use, the instrument enables grasping of tissue and diagnosis, illumination, imaging and/or treatment of target tissue positioned with the jaw cavity. That is, the device can provide surgical graspers integrated with a visualization probe such as fiber optic, confocal, optical tomography, etc. The jaws can enclose the tissue specimen within a confined space for interrogation with some form of light/imaging technology while protecting it from external light.

In the case of fluorescence, the working space and volume are reduced by confining the tissue within the jaw cavity which provides the ability to excite and visualize tissue in smaller volumes. It may also allow simultaneous visualization of white light (normal laparoscope) and fluorescence (locally in the cavity formed by jaw cups) in a single instrument and through a single port.

As can be appreciated, the probe in some embodiments can be utilized for illumination, imaging, diagnosis and/or treatment within the body cavity when the jaws are in the open position as well as within the confined space within the jaw cavity when the jaws are in the closed position.

Although shown within the abdominal cavity, the instrument can be used in other regions of the body.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical instrument for minimally invasive surgical procedures comprising:

a handle portion;

an elongated body portion extending distally from the handle portion;

an end effector extending distally of the elongated body portion and movable between an open position and a closed position;

an elongated tissue probe movably positioned within the elongated body portion for imaging tissue, the elongated tissue probe movable between a retracted position and an advanced position; and a sheath for receiving at least a portion of the elongated tissue probe therein, the sheath being directly coupled to the end effector, wherein movement of the sheath to a distal position causes movement of the elongated tissue probe to the advanced position and movement of the end effector from the open position to the closed position.

2. The surgical instrument of claim 1, wherein the end effector comprises first and second jaws, wherein at least one jaw of the first and second jaws has a cavity to receive tissue therein.

3. The surgical instrument of claim 2, wherein the elongated tissue probe is a visualization probe for imaging the tissue received within the cavity of the at least one jaw of the first and second jaws.

4. The surgical instrument of claim 2, wherein the sheath includes first and second posts in engagement with the first and second jaws to move the first and second jaws between the closed and open positions.

5. The surgical instrument of claim 1, wherein the end effector comprises first and second jaws and movement of the sheath to the distal position effects movement of the first and second jaws to the closed position.

6. The surgical instrument of claim 1, wherein the sheath includes an engagement structure configured for engaging the end effector to move the end effector between the open and closed positions.

7. The surgical instrument of claim 6, wherein the end effector comprises first and second jaws and the engagement structure includes a camming member engageable with the first jaw.

8. The surgical instrument of claim 1, wherein the elongated tissue probe is a light emitting illumination probe.

9. The surgical instrument of claim 1, wherein the end effector comprises first and second jaws forming a cavity therebetween when in the closed position to retain tissue therebetween and block out external light.

10. A surgical instrument for minimally invasive surgical procedures comprising:
   an actuator;
   an elongated portion extending distally from the actuator;
   first and second jaws extending distally of the elongated portion, at least one jaw of the first and second jaws having a tissue receiving cavity formed therein;
   a probe movably positioned within the elongated portion for imaging tissue positioned within the cavity when the first and second jaws are in a closed position; and
   a sheath for receiving at least a portion of the probe therein, the sheath being directly coupled to the first and second jaws, wherein distal movement of the sheath causes movement of the probe to an advanced position and causes the first and second jaws to be disposed in the closed position.

11. The surgical instrument of claim 10, wherein the probe is operably connected to the actuator, wherein actuation of the actuator moves the probe between a retracted position and the advanced position.

12. The surgical instrument of claim 10, wherein the first and second jaws are pivotally connected, and the first and second jaws are movable between an open position and the closed position.

13. The surgical instrument of claim 10, wherein the sheath is operatively connected to the actuator, and movement of the sheath from a proximal position to a distal position moves the probe from a retracted position to the advanced position.

* * * * *